(12) United States Patent
Kilgore et al.

(10) Patent No.: US 8,060,208 B2
(45) Date of Patent: Nov. 15, 2011

(54) ACTION POTENTIAL CONDUCTION PREVENTION

(75) Inventors: Kevin Kilgore, Avon Lake, OH (US); Niloy Bhadra, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 532 days.

(21) Appl. No.: 12/214,256

(22) Filed: Jun. 17, 2008

(65) Prior Publication Data
US 2008/0294221 A1 Nov. 27, 2008

Related U.S. Application Data

(63) Continuation-in-part of application No. 10/468,642, filed on Feb. 17, 2004, now Pat. No. 7,389,145.

(51) Int. Cl.
*A61N 1/34* (2006.01)

(52) U.S. Cl. ............................................. 607/46; 607/74

(58) Field of Classification Search .................. None
See application file for complete search history.

(56) References Cited

U.S. PATENT DOCUMENTS

| | | | |
|---|---|---|---|
| 6,421,566 B1 | 7/2002 | Holsheimer | |
| 2002/0055779 A1 | 5/2002 | Andrews | |
| 2002/0128694 A1* | 9/2002 | Holsheimer | 607/46 |
| 2004/0015203 A1* | 1/2004 | McGraw et al. | 607/48 |

* cited by examiner

*Primary Examiner* — Kennedy Schaetzle
(74) *Attorney, Agent, or Firm* — Kraguljac & Kalnay, LLC (57) ABSTRACT

An example method for selectively and reversibly preventing the conduction of action potentials in a targeted nerve region is presented. The method includes generating an electrical waveform having two phases and selectively depolarizing a nerve membrane using the electrical waveform. The nerve membrane is depolarized to a state where the nerve membrane cannot conduct an action potential. The depolarization is achieved by selectively repetitively providing the electrical waveform to a targeted nerve region associated with the nerve region to control m gates and h gates in the region and thus to control the availability of ions.

24 Claims, 9 Drawing Sheets

ACTION POTENTIAL CONDUCTION PREVENTION

CROSS REFERENCE TO RELATED APPLICATIONS

This application is a continuation in part of U.S. patent application Ser. No. 10/468,642 filed Feb. 17, 2004, now U.S. Pat. No. 7,389,145.

FEDERAL FUNDING NOTICE

The invention was developed with federal funding supplied under Federal Grant No. EB002091 provided by NIH National Institute of Biomedical Imaging and Bioengineering. The Federal government has certain rights in the invention.

COPYRIGHT NOTICE

A portion of the disclosure of this patent document contains material subject to copyright protection. The copyright owner has no objection to the facsimile reproduction of the patent document or the patent disclosure as it appears in the Patent and Trademark Office patent file or records, but otherwise reserves all copyright rights whatsoever.

BACKGROUND

Nerves conduct action potentials. Patents (e.g., Holsheimer U.S. Pat. No. 6,421,566) and publications (e.g., Grill et al, Stimulus Waveforms for Selective Neural Stimulation, IEEE Engineering in Medicine and Biology, 1995) have described biphasic pulses that partially depolarize a nerve membrane to facilitate activating a nerve.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

This application describes apparatus and methods for selectively preventing the conduction of action potentials through nerves in animals, including humans. Preventing the conduction of action potentials facilitates mitigating issues associated with uncontrolled and/or undesired muscle spasms. Muscle spasms may result from, for example, spinal cord injuries, stroke, cerebral palsy, multiple sclerosis, and so on. Preventing the conduction of action potentials also facilitates pain management associated, with for example, neuroma. Preventing the transmission of action potentials may even facilitate mitigating the effect of Tourette's Syndrome. Conventional nerve "blocking" techniques may have been non-reversible and/or may not have differentiated effects between large and small nerve fibers in a whole nerve. Additionally, conventional biphasic nerve stimulation techniques may have partially depolarized a nerve membrane to facilitate selectively stimulating the nerve using a controlled, desired voltage.

Example apparatus and methods provide electrical impulses through an implanted electrode that is located near, on, or in a nerve region. The electrode may be, for example, a tripolar electrode. The electrical impulses may be provided in different waveforms including sinusoidal waves, triangular waves, and rectangular waves. The electrical impulses may be voltage controlled, current controlled, and so on. The electrical impulses cause the nerve membrane to become incapable of conducting an action potential. This is different from conventional approaches that partially depolarize a membrane to facilitate later activation at a desired voltage and/or current. The mechanisms of sodium ion channels described below explain this effect. The effect is immediately and completely reversible. Example apparatus and methods may selectively block larger (motor) nerve fibers within a mixed nerve while allowing sensory information to travel through smaller (sensory) nerve fibers.

Figure 1:
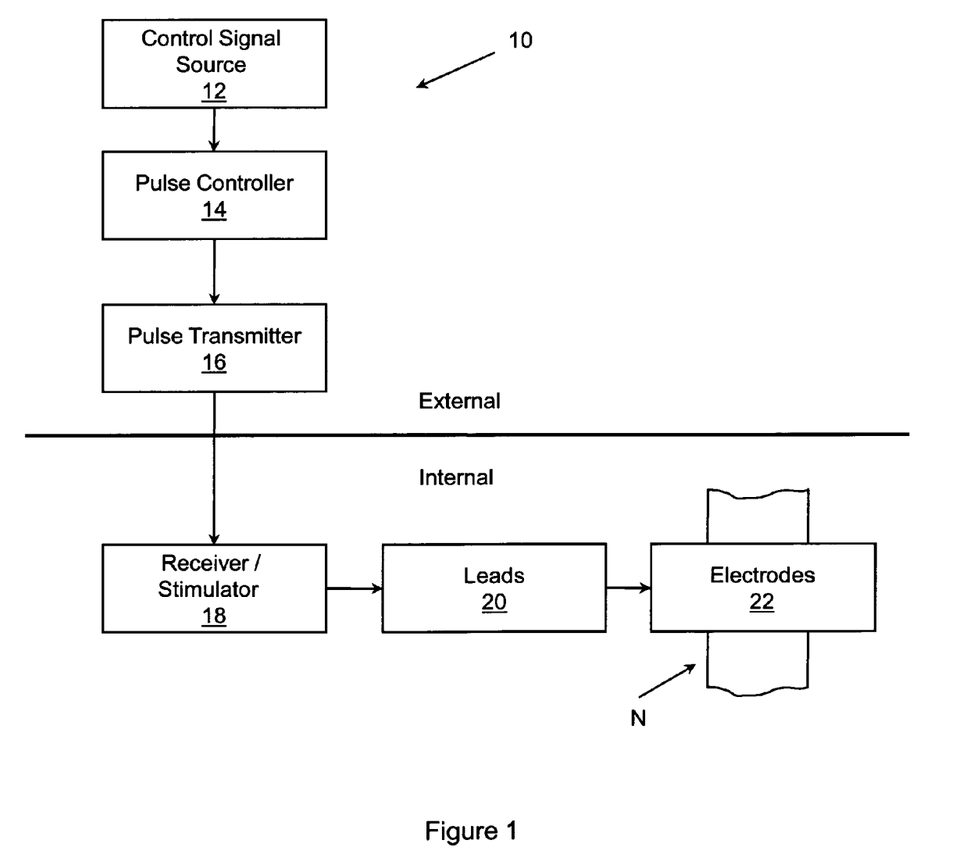
FIG. 1 is block diagram of a system that generates an electrical waveform and provides the electrical waveform through an electrode to a targeted nerve region. The electrical waveform controls gates that release ions in the targeted nerve region to prevent the conduction of action potentials through the targeted nerve region.

FIG. 1 illustrates a system 10 that stimulates a targeted nerve region N. The stimulation prevents the conduction of action potentials through the targeted nerve region N. The prevention of conduction of action potentials is non-destructive and immediately reversible. System 10 generates and distributes specific electrical stimulus waveforms to a targeted nerve region N. The stimulation prevents the conduction of action potentials in the targeted nerve region N. The stimulation is provided by application of the waveforms near, on, or in the targeted nerve region N. The waveforms may be applied through a nerve cuff electrode, a nerve hook electrode, an intramuscular electrode, a surface electrode on a muscle, a surface electrode on the skin near a nerve region, and so on. In a preferred embodiment, the electrode is a tripolar electrode that is wrapped around the nerve associated with targeted nerve region N.

System 10 includes a control signal source 12, a pulse controller 14, a pulse transmitter 16, a receiver/stimulator 18, an electrical lead(s) 20, and an electrode(s) 22. Control signal source 12 generates an output in response to a control signal. In one example, a control signal may be supplied by a user and thus the control signal source 12 may be a user-activatable control (e.g., push button). In another example, the control signal source 12 may be a myoelectric surface electrode applied to a skin surface that may detect an impending spasm based upon pre-established criteria. In this example, the control signal source 12 may automatically generate an output (e.g., control signal) without a volitional act by a user. In response to the output, the pulse controller 14 may generate a prescribed electrical stimulus waveform.

The pulse transmitter 16 transmits the prescribed electrical stimulus waveform to the receiver/stimulator 18. The pulse transmitter 16 also provides an electrical operating potential to the receiver/stimulator 18. The receiver/stimulator 18 distributes the waveform through the lead(s) 20 to the electrode (s) 22. The electrode(s) 22 stores electrical energy from the electrical operating potential and applies the electrical signal waveform to the targeted nerve region N. Applying the electrical signal waveform inhibits activity (e.g., conduction of action potentials) in the nerve fibers in the targeted nerve region.

In one example, the control signal source 12, the pulse controller 14, and the pulse transmitter 16 are external units located outside the body. In this example, the receiver/stimulator 18, the lead(s) 20, and the electrode(s) 22 may be implanted in the body in which the targeted nerve region N appears. In this example, the pulse transmitter 16 may be a transmitting coil that is secured to a skin surface over the receiver/stimulator 18. In this example, the pulse transmitter 16 transmits the waveform and power through the skin to the receiver/stimulator 18 in the form of radio frequency carrier waves. Because the implanted receiver/stimulator 18 receives power from the external pulse controller 14 through the external pulse transmitter 16, the implanted receiver/stimulator 18 does not require a dedicated battery power source.

Figure 2:
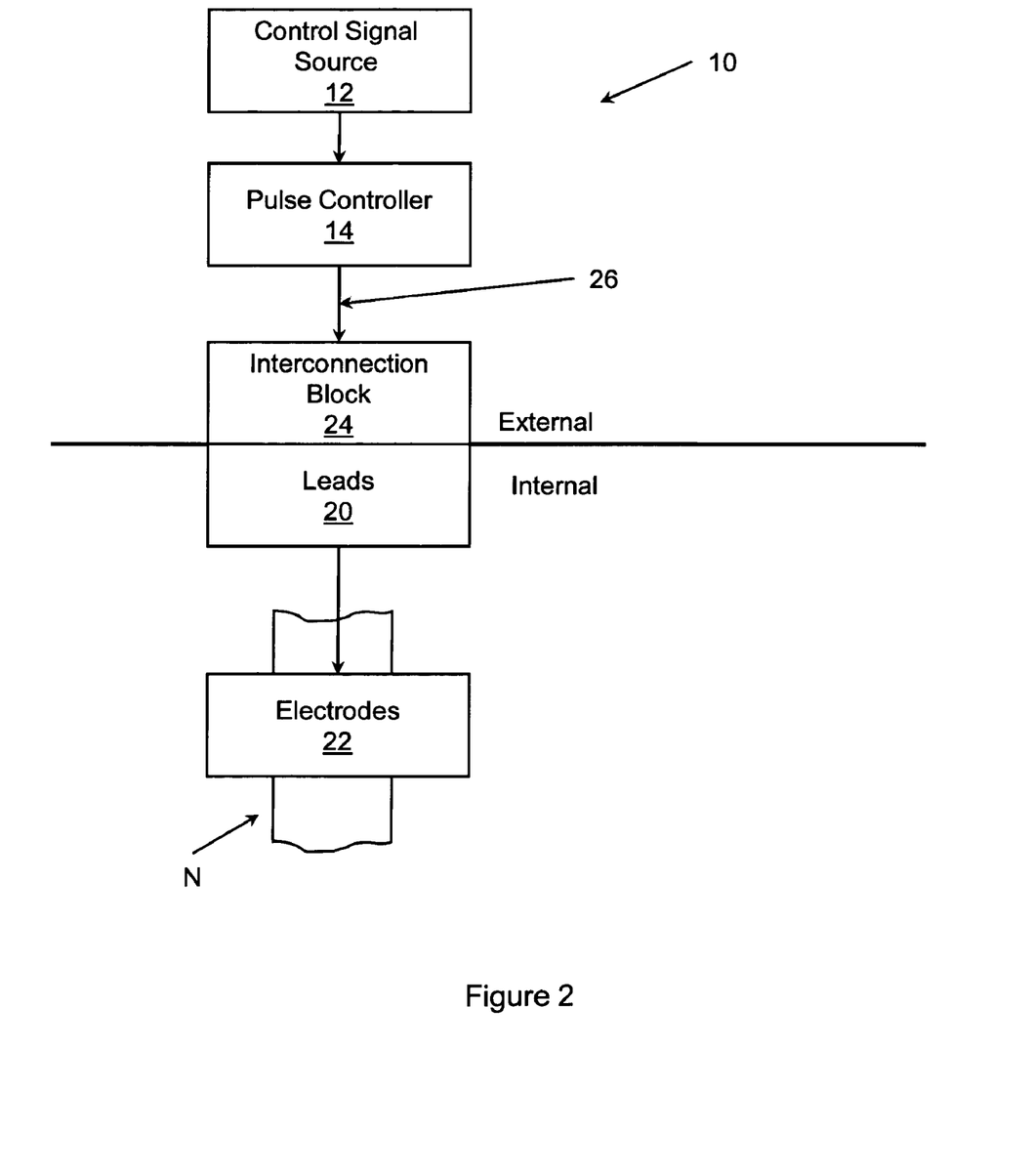
FIG. 2 is block diagram of a system that generates an electrical waveform and provides the electrical waveform through an electrode to a targeted nerve region. The electrical waveform controls gates that release ions in the targeted nerve region to prevent the conduction of action potentials through the targeted nerve region.

In another example, as illustrated in FIG. 2, the lead(s) 20 may be percutaneously installed and coupled to an external interconnection block 24. In this example the pulse controller 14 is coupled by a cable assembly 26 to the interconnection block 24. In this example, the pulse transmitter 16 and receiver/stimulator 18 may be omitted.

In one example, the pulse controller 14 may be housed in a compact, lightweight, hand held housing. The pulse controller 14 may include a microprocessor. The microprocessor may be configured with firmware, software, application specific integrated circuits, and so on, that when executed control generation of a desired electrical stimulation waveform. The waveform may be generated in response to input from the control signal source 12.

Figure 3:
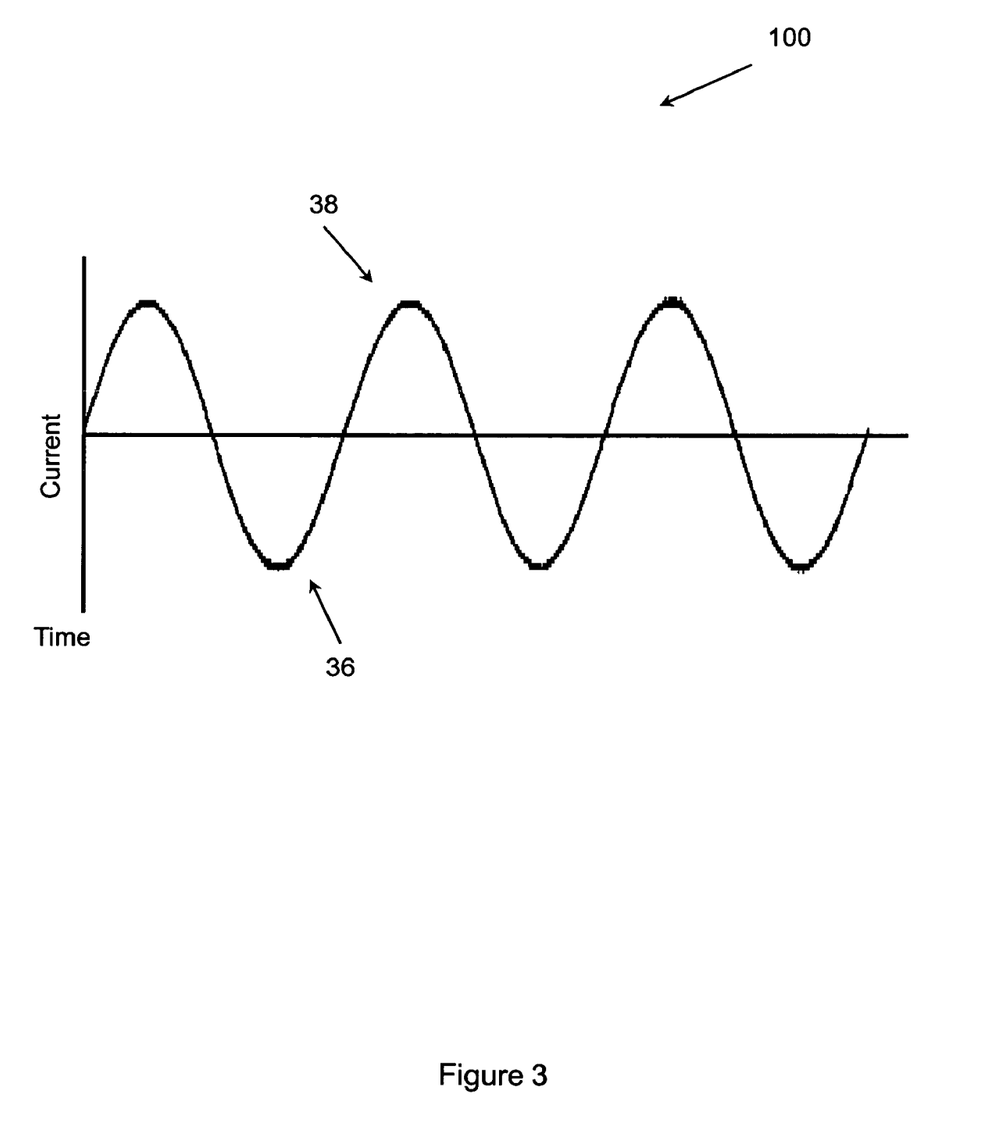
FIG. 3 illustrates a sinusoidal stimulation waveform having a constant current, a depolarizing cathodic pulse, and an anodic pulse.
Figure 4:
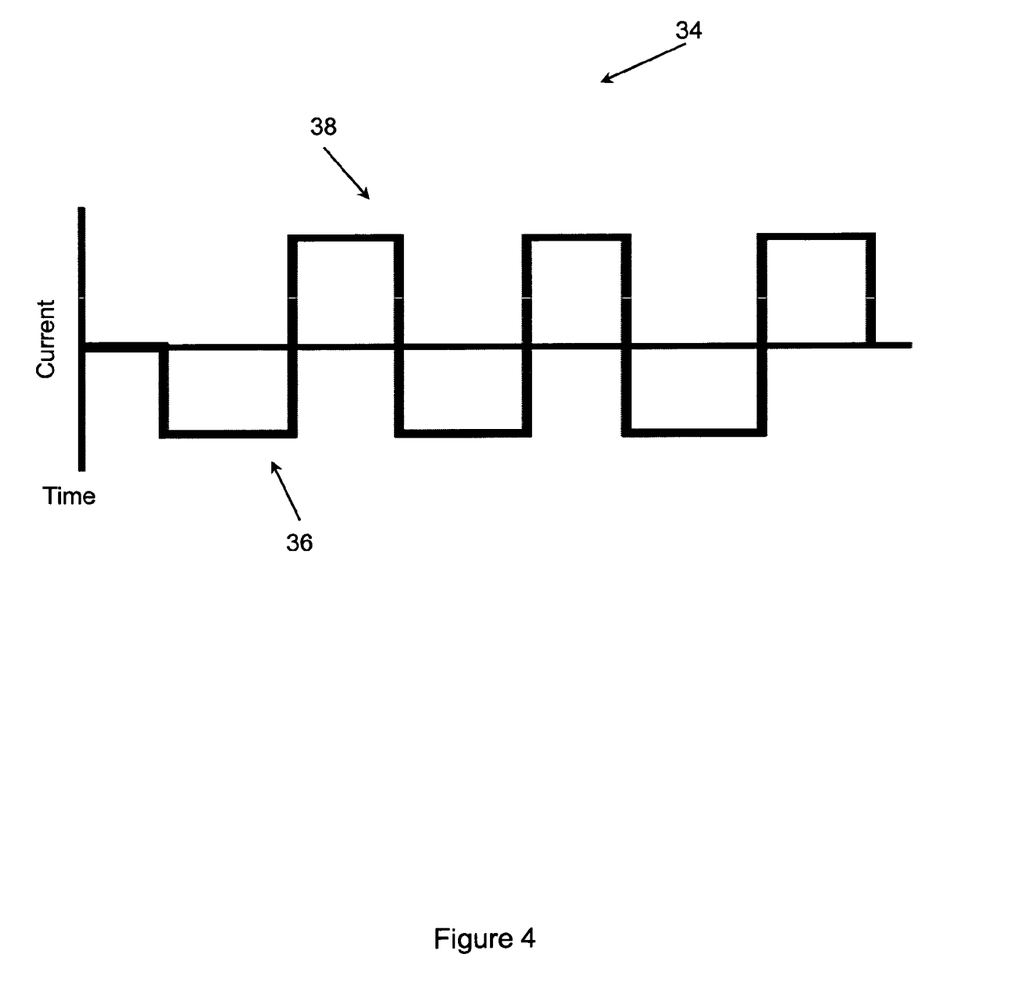
FIG. 4 illustrates a rectangular stimulation waveform having a constant current, a depolarizing cathodic pulse, and an anodic pulse.

FIG. 3 illustrates a sinusoidal waveform 100. FIG. 4 illustrates a rectangular waveform 34. Waveform 34 provides a stimulus that is delivered to a targeted nerve region N through electrodes located on or around a nerve. Waveform 34, or the other waveforms described herein (e.g., sinusoidal waveform 100 (FIG. 3), triangular waveform) when applied, cause a nerve fiber membrane to enter a state in which the nerve fiber membrane is unable to conduct action potentials. Waveform 34 has at least two phases. In one example, waveform 34 has a depolarizing phase 36 and a re-polarizing phase 38. Waveform 100 may have similar depolarizing and re-polarizing phases. Phase 36 cause depolarization of the nerve membrane through a low amplitude cathodic pulse. Phase 36 may be, for example, a shaped cathodic pulse with a duration of 0.1 to 1000 milliseconds and a variable amplitude between 0 and 1 milliamps. One skilled in the art will appreciate that other durations and amplitudes and combinations thereof may be employed. As illustrated through FIGS. 3 and 4, and as described herein, phase 36 can have various shapes. For example, phase 36 may be a square pulse, a ramped shape pulse, and so on. The pulses, or the rising or falling edges of the pulses, can present various linear, exponential, hyperbolic, quasi-trapezoidal, and other shapes.

Phase 38 provides an anodic current. In one example, anodic phase 38 has a higher amplitude than depolarizing phase 36 and has a shorter duration than depolarizing phase 36. Phase 38 may balance the charge of the phase 36. For example, the total charge in the phase 38 can be equal to but opposite to the charge in phase 36. In one example, the phase 38 may have a higher amplitude and shorter duration than phase 36. However, the phase 38 need not exactly balance the charge of the phase 36. The ratio of the absolute value of the amplitudes of the phase 38 compared to the phase 36 can be, for example, 1.0 to 5.0. One skilled in the art will appreciate that other ratios are possible. Because of the short duration of the anodic phase 38, the nerve membrane does not completely recover to the non-polarized state.

Biphasic pulses may be repeated to produce the stimulus waveform that causes the nerve to be unable to transmit action potentials in the region where the biphasic pulses are applied. In one example the stimulus waveform may be continuous. In another example, the stimulus waveform may be discontinuous and have breaks between phases. In one power efficient waveform there may be a break between the phase 36 and the phase 38. One skilled in the art will appreciate that various continuous and non-continuous waveforms may be employed. The pulse rate may vary depending on the duration of each phase. In one example the pulse rate may be in the range of 0.5 KHz up to 10 KHz. In another example, the pulse rate may be in the range of 1.0 KHz to 100 KHz. One skilled in the art will appreciate that other ranges may be possible. When waveform 34 is delivered at an appropriate rate, the nerve membrane is rendered incapable of transmitting an action potential. However, ceasing the application of the waveform 34 substantially instantaneously (e.g., within one activation refractory period) returns the action potential transmission capability of the nerve membrane.

Larger nerve fibers have a lower threshold for membrane depolarization. Therefore larger nerve fibers may be prevented from transmitting action potentials in response to the application of stimulus having amplitudes that are insufficient to prevent the transmission of action potentials in smaller nerve fibers. Thus it is possible to prevent the transmission of action potentials through larger nerve fibers in a nerve while allowing the transmission of action potentials through smaller fibers. At higher stimulus amplitudes, various sizes of fibers can be prevented from transmitting action potentials.

Figure 5:
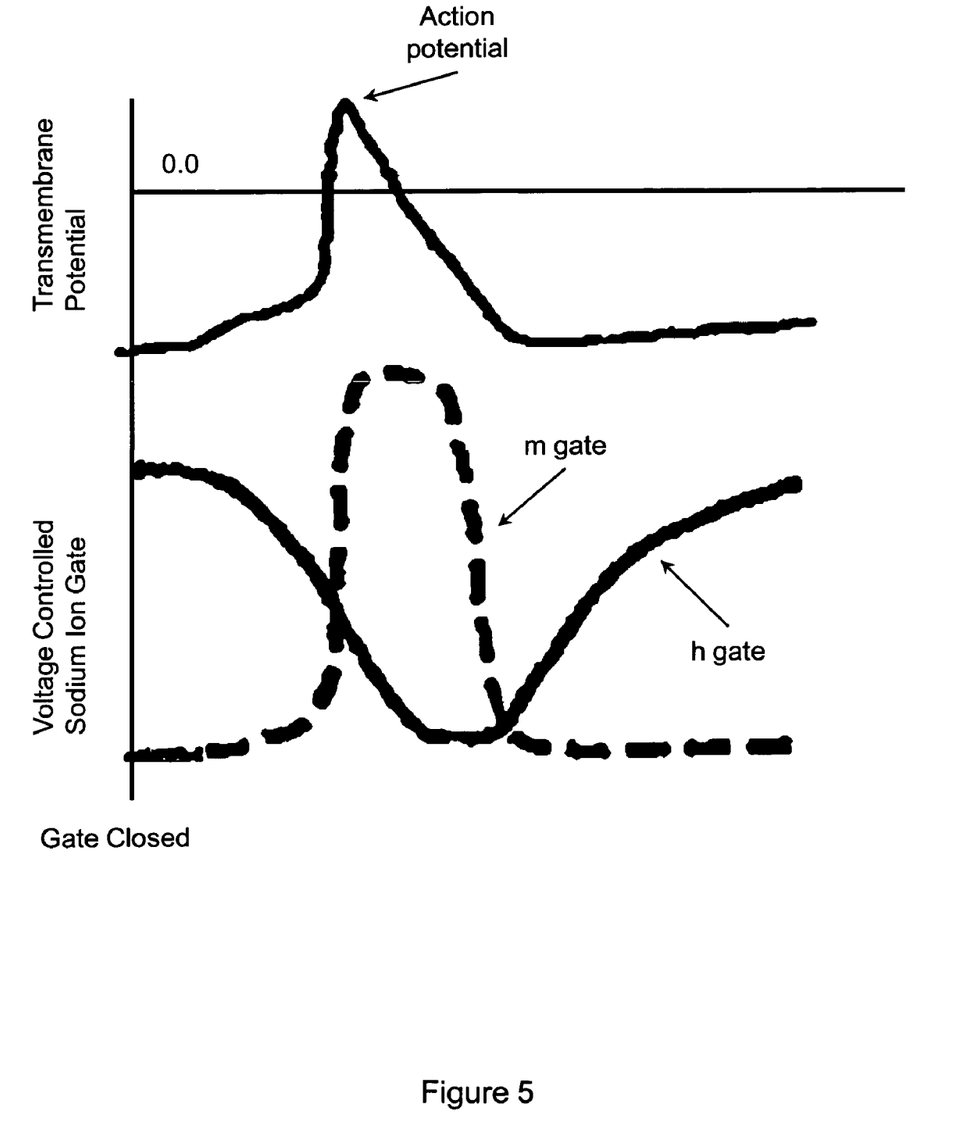
FIG. 5 illustrates actions of voltage controlled sodium ion gates during propagation of an action potential along a nerve. The top trace shows the trans-membrane potential and the bottom trace shows the activity of the sodium gates during the same time period. The action potential begins when the m gates open completely.

Sodium gating parameters illustrated in FIG. 5 provide information concerning how the transmission of action potentials may be prevented. A nerve axon may transmit signals due to the presence of voltage controlled ion channels. The function of the sodium ion channels are influenced by two gates. One gate responds quickly to voltage changes and is frequently termed the "m" gate. The other gate responds more slowly to voltage changes and is termed the "h" gate. While a single m gate and a single h gate are described, one skilled in the art will appreciate that more generally m gates and h gates may be discussed. When a nerve is in the rest condition, the m gates are almost completely closed while the h gates are partially opened. When an action potential propagates along an axon, the m gates open rapidly which produces a rapid depolarization of the nerve membrane. The h gates respond by slowly closing. The membrane begins to re-polarize and the m gates begin to close rapidly. At the end of action potential generation, the m gates have returned to their initial state and the nerve membrane is slightly more polarized than at rest. The h gates return more slowly to their resting values, which produces a period of reduced excitability that may be referred to as the refractory period. The same series of events can be initiated by an externally applied cathodic (depolarizing) stimulus pulse. Repeated applications of depolarizing stimulus followed by re-polarizing stimulus can prevent the conduction of an action potential by controlling the opening and closing of the h gates and the m gates and thus controlling the availability of sodium ions for polarization.

Figure 6:
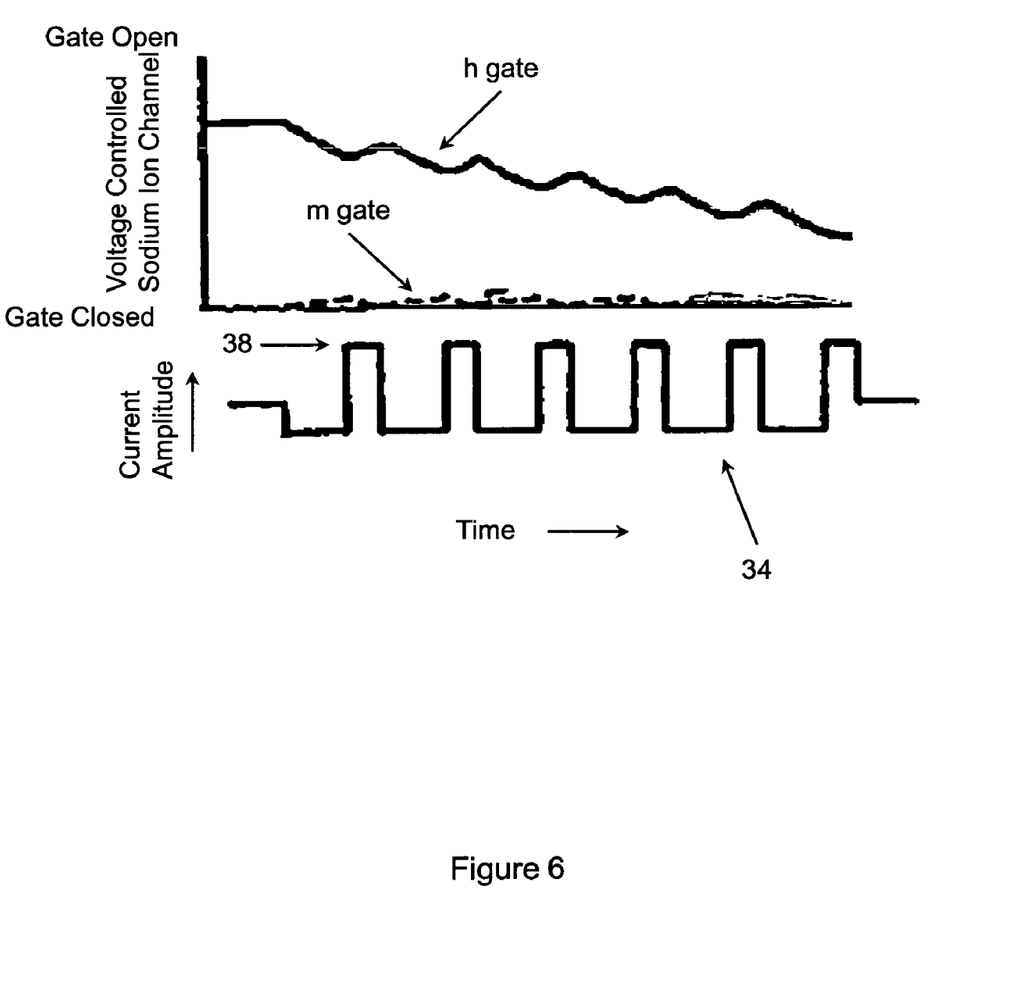
FIG. 6 illustrates the action of the depolarizing waveforms of FIGS. 3 and 4. The action is also shown in FIG. 6, below the upper graph, on the nerve membrane dynamics. The first pulse causes the h gate to close and then causes the m gate to open slightly. The second phase, which is shorter in duration, causes the m gate to return to the fully open state. Because the h gate responds more slowly it does not return completely to its resting value. As subsequent pulses are delivered, the h gate progressively closes, which causes the membrane to become inactivated. When the h gate is sufficiently closed, the nerve membrane can no longer conduct an action potential.

Waveform 34 uses the different relative responses of the two types of sodium ion channel gates to create a condition in a nerve where the nerve is prevented from transmitting action potentials in the region where the waveform 34 is applied. The phase 36 of the waveform 34 is a depolarizing pulse. The nerve membrane response is shown in FIG. 6. The h gates begin to slowly close during the phase 36 while the m gates respond by only opening slightly. As long as the initial phase is maintained at a desired level (e.g., below the activation threshold for the nerve), the m gates will exhibit only a small response. If the depolarizing phase 36 is maintained for long periods of time, the h gates will eventually close to the point that the membrane is no longer able to transmit an action potential. The membrane will be unable to conduct an action potential because insufficient ions will be available to produce conditions under which the action potential can be transmitted.

The phase 38 of the waveform 34 is a hyperpolarizing pulse. The hyperpolarizing phase 38 may be of shorter duration than the depolarizing phase 36. The effect of phase 38 is to cause the m gates to close completely and to cause the h gates to begin to open slowly. Since phase 38 may be shorter than phase 36, the h gates may not return to their resting levels by the end of phase 38. A second presentation of waveform 34 is then delivered to the nerve. The second presentation of waveform 34 may have the same shape as the first presentation of waveform 34. The depolarization caused by this iteration of the phase 36 results in further closing of the h gates and also yields slight opening of the m gates. Some opening of the h gates again occurs with the second hyperpolarizing phase 38 of the second presentation. While some opening of the h gates occurs, recovery back to the initial value does not occur. With further subsequent presentations, the h gates progressively near complete closing while the m gates vary slightly between fully closed and slightly open. The h gates will not fully close but will continue to oscillate with each pulse near the fully closed condition. With both the m gates and the h gates nearly closed, the nerve membrane becomes incapable of conducting action potentials.

The condition where action potentials cannot be conducted can be maintained indefinitely by continuously delivering pulses to the nerve. The condition is quickly reversible when the stimulation is stopped. The h gates and m gates will return to their resting values within a few milliseconds, and the nerve will again be able to transmit action potentials.

As described above, larger nerve fibers have a lower threshold for depolarization. Therefore, when a specific depolarizing waveform is delivered to a whole nerve, the largest nerve fibers may become incapable of transmitting action potentials while smaller fibers may remain capable of transmitting action potentials. Thus, example systems and methods facilitate selectively preventing the transmission of action potentials. The selective prevention may facilitate restricting motor activation without affecting sensory information. Example systems and methods may also prevent the transmission of action potentials in smaller nerve fibers in a large nerve. The prevention can be achieved by increasing the amplitude of the waveform. As the amplitude is increased, the first phase of the waveform may produce a stimulated action potential in the larger nerves. Example apparatus and methods may gradually increase the stimulus amplitude over time in subsequent pulses to prevent the transmission of action potentials in progressively smaller nerve fibers. Example apparatus and methods may increase the stimulus amplitude until even the smallest nerve fibers are prevented from transmitting action potentials.

Figure 7:
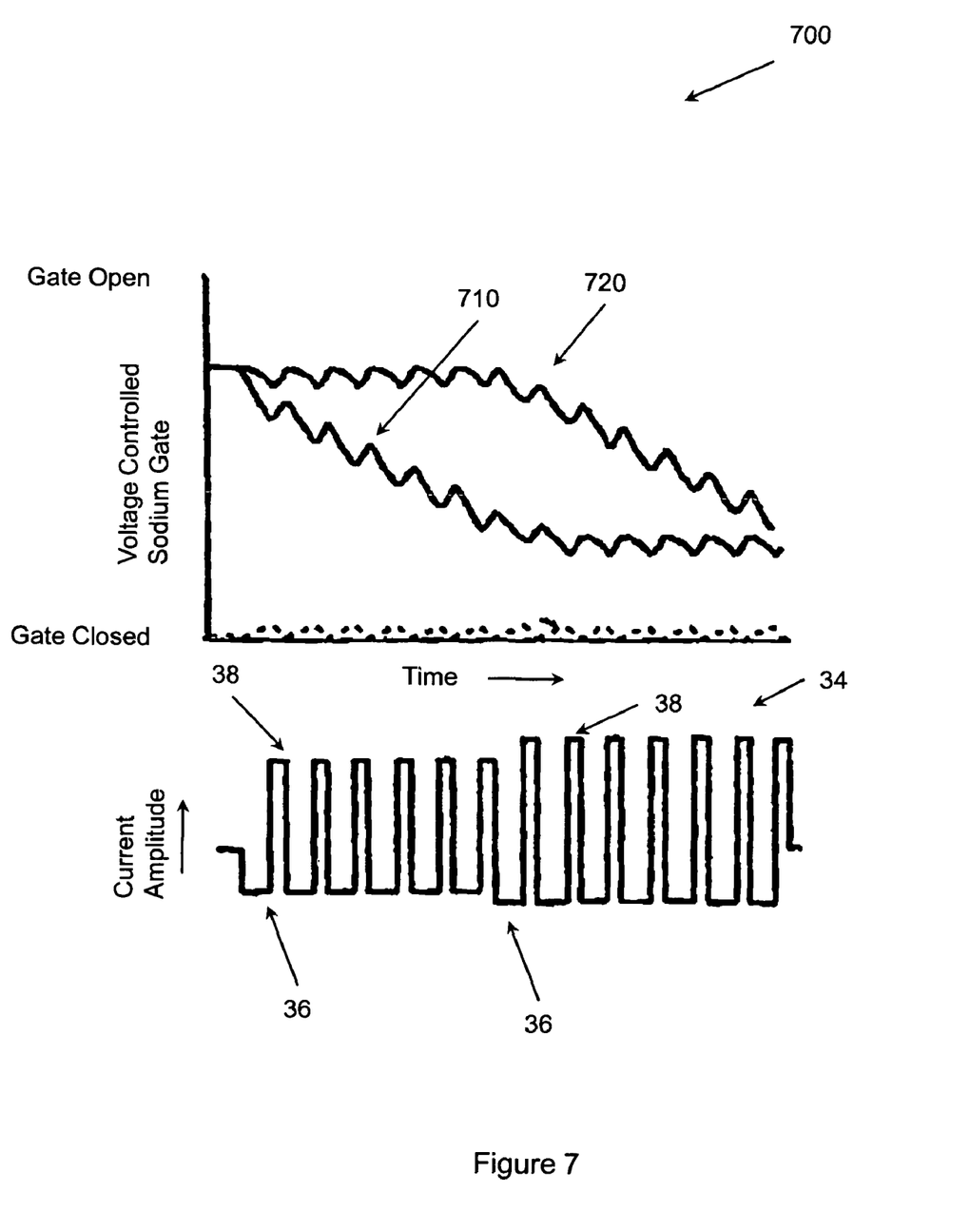
FIG. 7 illustrates two different nerve fiber diameters being progressively prevented from conducting action potentials. The larger fiber responds to the lower amplitude depolarizing pulse shown in the lower half of the diagram. The h gate is closed by this waveform and the large nerve fiber becomes inactive. The stimulus amplitude can then be increased so that inactivation of the smaller fiber can take place.

FIG. 7 illustrates using low amplitude pulses to put the membrane of relatively larger nerve fibers into an unexcitable state over the course of a few pulses. Once these larger fibers are at a steady state, they will not be activated even by large cathodic pulses. At this point, the stimulus amplitude can be increased so that it produces the closed h gate and closed m gate response in relatively smaller nerve fibers. The amplitude can be progressively increased until substantially all nerve fibers are prevented from transmitting action potentials. This progressive amplitude increase can occur at different rates. In one example, the progressive amplitude increase occurs within a few hundred milliseconds. The excitability of larger fibers is illustrated by 710 and the excitability of smaller fibers is illustrated by 720.

Returning now to FIG. 1, in one example, the control signal source 12 may comprise an electrode to sense electroneurogram (ENG) activity in a region where muscle spasms occur. The electrode may be the stimulation electrode 22 itself or a separate ENG sensing electrode. The electrode detects ENG activity of a predetermined level above normal activity. For example, ten times normal ENG activity may identify a spasm episode. While ten times normal ENG activity is described, one skilled in the art will appreciate that other ranges may be employed. In one example, generation of a desired waveform may commence when the above normal ENG activity is sensed. The waveform may be generated for a prescribed period of time to block a spasm. In one example, the waveform may be generated for a minute. One skilled in the art will appreciate that other periods of time may be employed. In one example, waveform generation may be controlled by a manual on-off button to facilitate activating and/or suspending generation of the waveform.

In another example, system 10 may block finger flexure spasms due, for example, to a multiple sclerosis, stroke, or so on. In this example, epimysial and/or intramuscular electrodes 22 may be implanted to facilitate blocking conduction of impulses to finger flexure muscles. In one example the control signal source 12 may be a manual on-off button. In another example, the control signal source 12 may be an electrode that senses electromyogram (EMG) activity in the finger flexor muscles. In this example the electrode detects EMG activity during stimulated activation of the finger extensor muscles. Waveform generation may be commenced upon detecting that the EMG activity exceeds a pre-determined, configurable threshold. In one example the threshold may be 30% of maximum contraction level. One skilled in the art will appreciate that different thresholds may be employed. In one example, the threshold may be dynamically configurable.

In another example, the control signal source 12 may be a mechanical control device. The mechanical device may sense movement in a body region. For example, the mechanical device may sense movement in a shoulder, in a scapula, in a knee, and so on. Waveform generation may commence upon detecting a specific motion. For example, detection of scapular winging may commence generation of a waveform. Waveform generation may be terminated upon detecting another motion.

Figure 8:
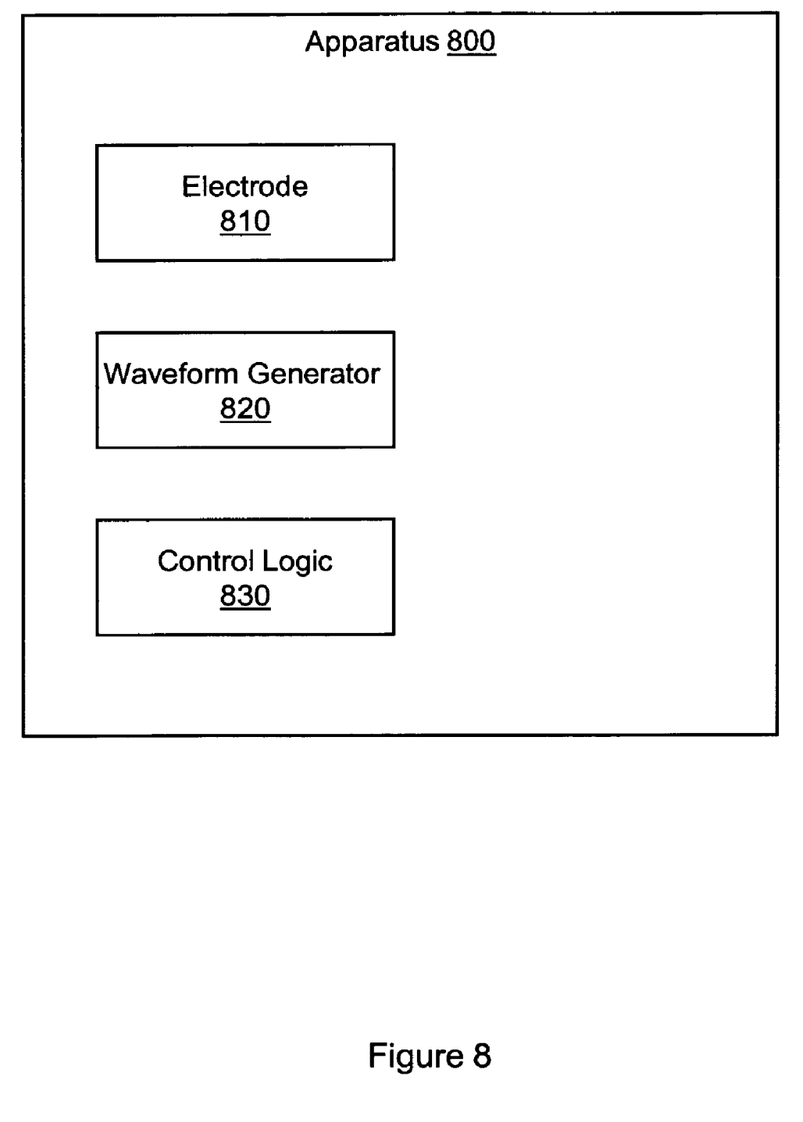
FIG. 8 illustrates an example apparatus that provides continued periodic delivery of two phases of an electrical waveform to a targeted nerve region to selectively and temporarily depolarize the nerve membrane in the targeted nerve region to a state where the targeted nerve region cannot conduct an action potential.

FIG. 8 illustrates an example apparatus 800 that provides continued periodic delivery of two phases of an electrical waveform to a targeted nerve region to selectively and temporarily depolarize the nerve membrane in the targeted nerve region to a state where the targeted nerve region cannot conduct an action potential. The targeted nerve region includes h gates and m gates, and the electrical waveform selectively controls the h gates and m gates to control the availability of ions in the targeted nerve region. Apparatus 800 includes an electrode 810 to deliver an electrical waveform to a targeted nerve region. Apparatus 800 also includes a waveform generator 820 to generate an electrical waveform having two phases. Continued periodic delivery of the two phases of the electrical waveform selectively and temporarily depolarizes the nerve membrane in the targeted nerve region to a state where the targeted nerve region cannot conduct an action potential. Apparatus 800 also includes a control logic 830 to control the waveform generator 820 to selectively generate the electrical waveform and to selectively provide the electrical waveform to the targeted nerve region through the electrode 810.

In one example, the two phases of the electric waveform include a de-polarizing phase and a hyper-polarizing phase. The hyper-polarizing phase may balance the de-polarizing phase. In one example, the electrode 810 may be a tripolar electrode that encircles the targeted nerve region. The control logic 830 may be configured to control the electrical waveform generated by the waveform generator 820 with respect to voltage, current, waveform shape, phase duration, frequency, period, amplitude, and so on. In one example, the electrical waveform has a frequency of from 1 kilohertz (KHz) to 100 KHz.

Figure 9:
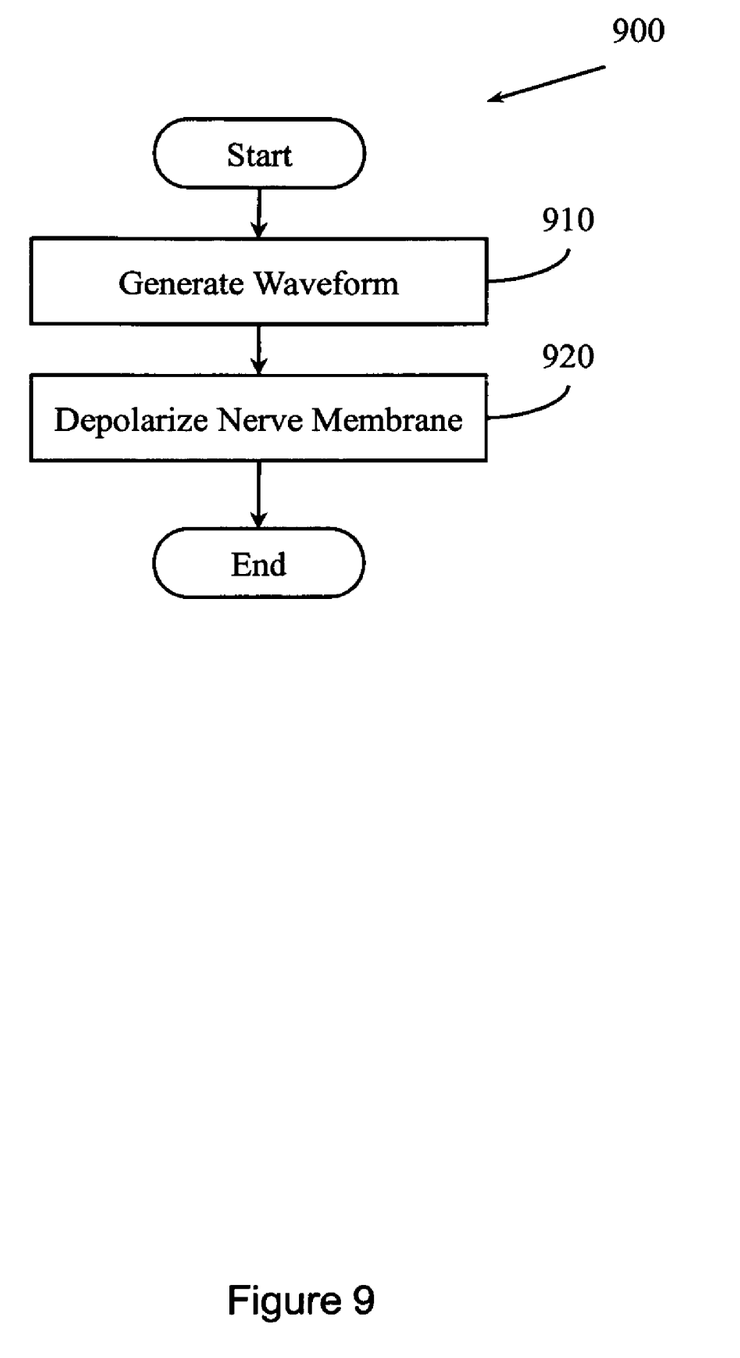
FIG. 9 illustrates an example method that provides continued periodic delivery of two phases of an electrical waveform to a targeted nerve region to selectively and temporarily depolarize the nerve membrane in the targeted nerve region to a state where the targeted nerve region cannot conduct an action potential.

FIG. 9 illustrates an example method 900 that provides continued periodic delivery of two phases of an electrical waveform to a targeted nerve region to selectively and temporarily depolarize the nerve membrane in the targeted nerve region to a state where the targeted nerve region cannot conduct an action potential. Method 900 includes, at 910, generating an electrical waveform having two phases. Method 900 also includes, at 920, selectively depolarizing a nerve membrane to a state where the nerve membrane cannot conduct an action potential by selectively repetitively providing the electrical waveform to a targeted nerve region associated with the nerve region.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

While example apparatus, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, AAB, AABB, AABBC, AABBCC, and so on (e.g., the data store may store only A, only B, only C, A&B, A&C, B&C, A&B&C, A&A&A, A&A&B, A&A&B&B, A&A&B&B&C, A&A&B&B&C&C, and so on). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:
1. An apparatus, comprising:
an electrode to deliver an electrical waveform to a targeted nerve region;
a waveform generator to generate the electrical waveform, where the electrical waveform has two phases, and where the continued periodic delivery of the two phases of the electrical waveform selectively and temporarily depolarizes the nerve membrane in the targeted nerve region to a state where the targeted nerve region cannot conduct an action potential;
a control logic to control the waveform generator to selectively generate the electrical waveform and to selec- tively provide the electrical waveform to the targeted nerve region through the electrode; and an amplitude modulation logic to selectively control the amplitude of the electrical waveform to selectively prevent the transmission of action potentials in nerve fibers of different sizes, where the amplitude modulation logic is configured to progressively increase the amplitude of the electrical waveform to block progressively smaller nerves.

2. The apparatus of claim 1, where the two phases include a de-polarizing phase and a hyper-polarizing phase.

3. The apparatus of claim 2, where the hyper-polarizing phase balances the de-polarizing phase.

4. The apparatus of claim 1, the electrode being a tripolar electrode.

5. The apparatus of claim 4, the tripolar electrode encircling the targeted nerve region.

6. The apparatus of claim 1, the control logic being configured to control the electrical waveform generated by the waveform generator with respect to one or more of, voltage, and current.

7. The apparatus of claim 1, where the electrical waveform shape is one of, a rectangular shape, a sinusoidal shape, and a triangular shape.

8. The apparatus of claim 1, where the electrical waveform is a continuous waveform.

9. The apparatus of claim 1, where the electrical waveform is a discontinuous waveform.

10. The apparatus of claim 1, where the electrical waveform has a frequency of from 1 kilohertz (KHz) to 100 KHz.

11. The apparatus of claim 1, where the amplitude modulation logic is configured to progressively increase the amplitude of the electrical waveform to block progressively smaller nerves to facilitate restricting motor activation without affecting sensory information.

12. The apparatus of claim 1, where the electrical waveform is configured to treat pain.

13. A method, comprising:
generating an electrical waveform having two phases;
selectively depolarizing a nerve membrane to a state where the nerve membrane cannot conduct an action potential by selectively repetitively providing the electrical waveform to a targeted nerve region associated with the nerve region; and
selectively controlling the amplitude of the electrical waveform to selectively prevent the transmission of action potentials, where selectively controlling the amplitude of the electrical waveform comprises progressively increasing the amplitude of the electrical waveform to block progressively smaller nerves.

14. The method of claim 13, where the two phases include a de-polarizing phase and a hyper-polarizing phase.

15. The method of claim 14, where the hyper-polarizing phase balances the de-polarizing phase.

16. The method of claim 13, where the electrical waveform is provided to the targeted nerve region via a tripolar electrode that encircles the targeted nerve region.

17. The method of claim 13, including selectively controlling one or more of, a voltage associated with the waveform, and a current associated with the waveform.

18. The method of claim 13, including selectively controlling the shape of the electrical waveform to be one of, a rectangular shape, a sinusoidal shape, and a triangular shape.

19. The method of claim 13, where the electrical waveform is provided as a continuous waveform.

20. The method of claim 13, where the electrical waveform is provided as a discontinuous waveform.

21. The method of claim 13, where the electrical waveform is provided at a frequency of from 1 KHz to 100 KHz, where the targeted nerve region includes h gates and m gates, and where the electrical waveform selectively controls the h gates and m gates to control the availability of ions in the targeted nerve region.

22. The method of claim 13, where selectively controlling the amplitude of the electrical waveform comprises progressively increasing the amplitude of the electrical waveform to block progressively smaller nerves to facilitate restricting motor activation without affecting sensory information.

23. The method of claim 13, where the electrical waveform is configured to treat pain.

24. An apparatus for treating pain, comprising:
an electrode to deliver a pain controlling electrical waveform to a targeted nerve region;
a waveform generator to generate the pain controlling electrical waveform, where the pain controlling electrical waveform has two phases, and where the continued periodic delivery of the two phases of the pain controlling electrical waveform selectively and temporarily depolarizes the nerve membrane in the targeted nerve region to a state where the targeted nerve region cannot conduct an action potential;
a pain control logic to control the waveform generator to selectively generate the pain controlling electrical waveform and to selectively provide the pain controlling electrical waveform to the targeted nerve region through the electrode; and
an amplitude modulation logic to selectively control the amplitude of the pain controlling electrical waveform to selectively prevent the transmission of action potentials in nerve fibers of different sizes.

* * * * *

UNITED STATES PATENT AND TRADEMARK OFFICE
CERTIFICATE OF CORRECTION

PATENT NO. : 8,060,208 B2  
APPLICATION NO. : 12/214256  
DATED : November 15, 2011  
INVENTOR(S) : Kevin L. Kilgore and Niloy Bhadra Page 1 of 1

It is certified that error appears in the above-identified patent and that said Letters Patent is hereby corrected as shown below:

Specification,  
Column 1, lines 13-17 in the section entitled FEDERAL FUNDING NOTICE, please replace Paragraph with the following:

--FEDERAL FUNDING NOTICE

This invention was made with government support under grant No. EB002091, awarded by the NIH-National Institute of Biomedical Imaging and Bioengineering. The government has certain rights in the invention.--

Signed and Sealed this  
Twenty-fourth Day of November, 2015

Michelle K. Lee  
*Director of the United States Patent and Trademark Office*